(12) United States Patent
Abel et al.

(10) Patent No.: US 7,708,945 B1
(45) Date of Patent: May 4, 2010

(54) DEVICE AND METHOD FOR DETERMINING MULTIPLE ANALYTES

(75) Inventors: Andreas Peter Abel, Basel (CH); Gert Ludwig Duveneck, Bad Krozingen (DE); Markus Ehrat, Magden (CH); Gerhard Matthias Kresbach, Staufen (DE); Michael Pawlak, Laufenburg (DE); Eveline Schürmann-Mader, Zeihen (CH)

(73) Assignee: Bayer Technology Services GmbH, Leverkusen (DE)

( * ) Notice: Subject to any disclaimer, the term of this patent is extended or adjusted under 35 U.S.C. 154(b) by 870 days.

(21) Appl. No.: 10/030,972

(22) PCT Filed: Aug. 3, 2000

(86) PCT No.: PCT/EP00/07529

§ 371 (c)(1),
(2), (4) Date: Jan. 15, 2002

(87) PCT Pub. No.: WO01/13096

PCT Pub. Date: Feb. 22, 2001

(30) Foreign Application Priority Data

Aug. 13, 1999 (CH) .................................. 1486/99

(51) Int. Cl.
*G01N 21/00* (2006.01)
*G01N 31/22* (2006.01)
(52) U.S. Cl. .............................. 422/58; 422/55; 422/57; 422/82.11; 422/82.05; 422/68.1; 435/283.1; 435/287.1; 435/7.1; 435/287.2; 435/288.7
(58) Field of Classification Search ..................... 435/4, 435/6, 7.1, 40.5, 283.1, 287.1, 287.2, 288.7; 385/12, 31, 37, 52; 422/55, 82.11, 82.05, 422/68.1, 61, 57, 58
See application file for complete search history.

(56) References Cited

U.S. PATENT DOCUMENTS 4,649,280 A    3/1987    Holland et al.

(Continued)

FOREIGN PATENT DOCUMENTS

DE    44 10 258 A1    10/1994

(Continued)

OTHER PUBLICATIONS

Warren C.W. Chan and Shuming Nie, "Quantum Dot Bioconjugates for Ultrasensitive Nonisotopic Detection", *Science*, vol. 281, Sep. 25, 1998, pp. 2016-2018.

(Continued)

*Primary Examiner*—Melanie J Yu
(74) *Attorney, Agent, or Firm*—Wenderoth, Lind & Ponack, L.L.P.

(57) ABSTRACT

A device includes a planar optical waveguide, as part of a sensor platform, and, connected to the platform directly or by means of a sealing medium, a sealing layer. The sealing layer forms either directly or by means of a sealing medium a tightly sealing layer. The sealing layer includes a multitude of recesses at least open towards the sensor platform, which form a corresponding multitude of sample compartments in a 2-dimensional arrangement. Each of the sample compartments has different biological or biochemical recognition elements, for the specific recognition and binding of different analytes, immobilized in five or more discrete measurement areas, wherein the measurement areas are in optical interaction with excitation light emanating from the optical waveguide, as part of the sensor platform which forms a demarcation of the sample compartments, and wherein the sample compartments are operable to be cleared from received sample or reagent solutions and to then receive, optionally without washing steps, further sample or reagent solutions, which are supplied to the same sample compartments.

75 Claims, 1 Drawing Sheet

U.S. PATENT DOCUMENTS

| | | | |
|---|---|---|---|
| 4,978,503 | A | 12/1990 | Shanks et al. |
| 5,006,716 | A | 4/1991 | Hall |
| 5,432,099 | A | 7/1995 | Ekins |
| 5,459,325 | A | 10/1995 | Hueton et al. |
| 5,478,755 | A | 12/1995 | Attridge et al. |
| 5,738,825 | A | 4/1998 | Rudigier et al. |
| 5,747,274 | A | 5/1998 | Jackowski |
| 5,807,755 | A | 9/1998 | Ekins |
| 5,837,551 | A | 11/1998 | Ekins |
| 5,841,143 | A | 11/1998 | Tuma et al. |
| 6,192,168 | B1 * | 2/2001 | Feldstein et al. ............... 385/12 |
| 6,329,209 | B1 * | 12/2001 | Wagner et al. ............... 436/518 |
| 6,342,349 | B1 * | 1/2002 | Virtanen ........................ 435/6 |
| 6,395,558 | B1 * | 5/2002 | Duveneck et al. ........... 436/172 |
| 6,480,639 | B2 * | 11/2002 | Hashimoto et al. ............ 385/14 |
| 6,660,233 | B1 * | 12/2003 | Coassin et al. ............... 422/104 |

FOREIGN PATENT DOCUMENTS

| | | |
|---|---|---|
| EP | 0 872 735 A1 | 10/1998 |
| GB | 2 276 635 | 10/1994 |
| WO | 84/01031 | 3/1984 |
| WO | 93/25892 | 12/1993 |
| WO | 94/27137 | 11/1994 |
| WO | 95/33197 | 12/1995 |
| WO | 95/33198 | 12/1995 |
| WO | 96/35940 | 11/1996 |
| WO | 97/35203 | 9/1997 |
| WO | 97/46707 | 12/1997 |
| WO | 98/09156 | 3/1998 |
| WO | 98/22799 | 5/1998 |
| WO | 99/36766 | 7/1999 |

OTHER PUBLICATIONS

Kristina A. Cole, David B. Krizman and Michael R. Emmert-Buck, "The Genetics of Cancer-a 3D Model", *Nature Genetics Supplement*, vol. 21, Jan. 1999, pp. 38-41.

K. Tiefenthaler and W. Lukosz, "Sensitivity of Grating Couplers as Integrated-Optical Chemical Sensors", *Journal of the Optical Society of America*, vol. 6, No. 2, Feb. 1989, pp. 209-220.

W. Lukosz, Ph. M. Nellen, Ch. Stamm and P. Weiss, "Output Grating Couplers on Planar Waveguides as Integrated Optical Chemical Sensors", *Sensors and Actuators*, B1 (1990), pp. 585-588.

T. Tamir and S.T. Peng, "Analysis and Design of Grating Couplers", *Applied Physics*, 14 (1977), pp. 235-254.

D. Bovelli et al., "Highly Oriented, Self-Assembled Alkanephosphate Monolayers on Tantalum (V) Oxide Surfaces", *Langmuir*, 14 (1999), pp. 4324-4327.

* cited by examiner

Figure 1

DEVICE AND METHOD FOR DETERMINING MULTIPLE ANALYTES

The invention is related to a device comprising a multitude of sample compartments, wherein in each of the sample compartments different and binding of different analytes, are immobilized in five or more discrete measurement areas in these sample compartments. These biological or biochemical recognition elements in the measurement areas are immobilized either directly or by means of an adhesion promoting layer and, optionally, still further layers on the surface of an optical waveguide, as part of a sensor platform, which surface forms a demarcation of the sample compartments. Thereby, the sensor platform can be provided in different embodiments.

The invention is also related to an analytical system comprising a device with different embodiments of the sensor platform, an optical system for the determination of luminescence with at least one excitation light source and at least one detector for the detection of the light emanating from the measurement areas, and supply means for bringing one or more samples into contact with the measurement areas on the sensor platform. Further objects of the invention are methods for the detection of luminescence using sensor platforms, optical systems and analytical systems, and the use of these methods for quantitative affinity sensing and other applications.

The object of this invention is to provide measurement configurations with a multitude of small-volume sample compartments allowing for the simultaneous, highly sensitive determination of a multitude of analytes.

For the determination of a multitude of analytes, currently such methods are mainly used, wherein the determination of different analytes is performed in discrete sample compartments or "wells" of so-called microtiter plates. The most common are plates with a pitch (geometrical arrangements in rows and columns) of 8×12 wells on a footprint of typically about 8 cm×12 cm, wherein a volume of some hundred microliters is required for filling a single well. It would be desirable for many applications, however, to determine multiple analytes in a single sample compartment, upon using a sample volume that is as small as possible.

In U.S. Pat. No. 5,747,274, measurement arrangements and methods for the early recognition of a cardiac infarction, upon determination of at least three infarction markers, are described. The determination of these markers can be performed in individual sample compartments or in a common sample compartment, a single (common) sample compartment, according to the disclosure for the latter case, as a continuous flow channel, one demarcation of which being formed, for example, by a membrane, whereon antibodies for the three different markers are immobilized. However, there are no hints for an arrangement of several sample compartments or flow channels of this type on a common support. Additionally, there are no geometrical informations concerning the size of the measurement areas.

In WO 84/01031, U.S. Pat. No. 5,807,755, U.S. Pat. No. 5,837,551, and in U.S. Pat. No. 5,432,099, immobilization of the specific recognition elements for an analyte in the geometry of small "spots", of partially significantly below 1 mm$^2$, on a solid support is proposed. The purpose of this immobilization geometry is to be able to determine the concentration of an analyte in a way which is only dependent from the incubation time, but essentially independent from the absolute sample volume (in the absence of a continuous flow), upon binding only a small part of the analyte molecules that are present. The measurement arrangements disclosed in the related examples are based on determinations by fluorescence measurements in conventional microtiter plates. Thereby, arrangements are also described wherein spots of up to three different, fluorescently labeled antibodies are measured in a common microtiter plate well. A minimization of the spot size would be desirable, following the theoretical argumentation in these patent specifications. The minimum signal height to be distinguished from the background signal, however, would set a lower limit for the spot size.

For achieving lower detection limits, in recent years numerous measurement arrangements have been developed, wherein the determination of an analyte is based on its interaction with the evanescent field, which is associated with light guiding in an optical waveguide, and wherein biochemical or biological recognition elements for the specific recognition and binding of the analyte molecules are immobilized on the surface of the waveguide.

When a light wave is coupled into a planar thin-film waveguide surrounded by optically rarer media, i.e., media of lower refractive index, the light wave is guided by total reflection at the interfaces of the waveguiding layer. In that arrangement, a fraction of the electromagnetic energy penetrates the media of lower refractive index. This portion is termed the evanescent (=decaying) field. The strength of the evanescent field depends to a very great extent on the thickness of the waveguiding layer itself and on the ratio of the refractive indices of the waveguiding layer and of the media surrounding it. In the case of thin waveguides, i.e., layer thicknesses that are the same as or smaller than the wavelength of the light to be guided, discrete modes of the guided light can be distinguished. As an advantage of such methods, the interaction with the analyte is limited to the penetration depth of the evanescent field into the adjacent medium being of the order of some hundred nanometers, and interfering signals from the depth of the (bulk) medium can be mainly avoided. The first proposed measurement arrangements of this type were based on highly multi-modal, self-supporting single-layer waveguides, such as fibers or plates of transparent plastics or glass, with thicknesses from some hundred micrometers up to several millimeters.

In U.S. Pat. No. 4,978,503, a measurement arrangement is disclosed, wherein a liquid sample is drawn into a cavity by capillary forces, wherein an optically transparent side wall is provided as a self-supporting multimode waveguide, and wherein at least on a part of the surface of that side wall ("patch") facing the cavity, a biochemical recognition element for the recognition and binding of an analyte from a sample is immobilized. Although the manufacturing of arrays with arrangements of several discrete patches is described, the further explanations teach that the patches are laterally separated from each other by connecting links, provided for the combination of the base plates with the cover plates of the capillaries, so that, after segregation of the array, each capillary contains only one patch of immobilized recognition elements. Additionally, as a disadvantage of this arrangement, an exchange of the liquid drawn into the capillary is not provided for, such an exchange, for example, desirable for a multi-step assay.

In WO 94/27137, measurement arrangements are disclosed, wherein "patches" with different recognition elements for the determination of different analytes are immobilized on a self-supporting optical substrate waveguide (single-layer waveguide), excitation light being incoupled at the distal surfaces ("front-face" or "distal end" coupling), wherein laterally selective immobilization is performed using photo-activatable cross-linkers. According to the disclosure, several patches can be arranged row-wise in common, parallel flow channels or sample compartments, and wherein the parallel flow channels or sample compartments extend over the whole length of the range on the waveguide used as a sensor in order to avoid an impairment of light guiding in the waveguide. However, there are no hints to a two-dimensional integration of multiple patches in sample compartments of relatively small size, i.e., significantly below 1 cm² base area. In a similar arrangement disclosed in WO 97/35203, several embodiments of an arrangement are described, wherein different recognition elements for the determination of different analytes are immobilized in separate, parallel flow channels or sample compartments for the sample and for calibration solutions of low and, optionally in addition, of high analyte concentration. Again, no hint is given how a high integration density of different recognition elements in a common compartment for receiving the sample could be achieved. Additionally, the sensitivity of highly multi-modal, self-supporting single-layer waveguides is not sufficient for many applications requiring the achieving of very low detection limits.

For an improvement of the sensitivity and simultaneously for an easier manufacturing in mass production, planar thin-film waveguides have been proposed. In the simplest case, a planar thin-film waveguide consists of a three-layer system: support material (substrate), waveguiding layer, superstrate (respectively the sample to be analyzed), wherein the waveguiding layer has the highest refractive index. Additional intermediate layers can further improve the action of the planar waveguide.

Several methods for the incoupling of excitation light into a planar waveguide are known. The methods used earliest were based on front face coupling or prism coupling, wherein generally a liquid is introduced between the prism and the waveguide, in order to reduce reflections due to air gaps. These two methods are mainly suited with respect to waveguides of relatively large layer thickness, i.e., especially self-supporting waveguides, and with respect to waveguides with a refractive index significantly below 2. For incoupling of excitation light into very thin waveguiding layers of high refractive index, however, the use of coupling gratings is a significantly more elegant method.

Different methods of analyte determination in the evanescent field of lightwaves guided in optical film waveguides can be distinguished. Based on the applied measurement principle, for example, it can be distinguished between fluorescence, or more general luminescence methods, on one side and refractive methods on the other side. In this context, methods for generation of surface plasmon resonance in a thin metal layer on a dielectric layer of lower refractive index can be included in the group of refractive methods, if the resonance angle of the launched excitation light for generation of the surface plasmon resonance is taken as the quantity to be measured. Surface plasmon resonance can also be used for the amplification of a luminescence or the improvement of the signal-to-background ratios in a luminescence measurement. The conditions for generation of a surface plasmon resonance and the combination with luminescence measurements, as well as with waveguiding structures, are described in the literature, for example in U.S. Pat. Nos. 5,478,755, 5,841,143, 5,006,716, and 4,649,280.

In this application, the term "luminescence" means the spontaneous emission of photons in the range from ultraviolet to infrared, after optical or other than optical excitation, such as electrical, chemical, biochemical or thermal excitation. For example, chemiluminescence, bioluminescence, electroluminescence, and especially fluorescence and phosphorescence are included under the term "luminescence".

In case of the refractive measurement methods, the change of the effective refractive index resulting from molecular adsorption to or desorption from the waveguide is used for analyte detection. This change of the effective refractive index is determined, in case of grating coupler sensors, from changes of the coupling angle for the in- or outcoupling of light into or out of the grating coupler sensor, in a case of interferometric sensors from changes of the phase difference between measurement light guided in a sensing branch and a referencing branch of the interferometer.

The state of the art for using one or more coupling gratings for the in- and/or outcoupling of guided waves is described, for example, in K. Tiefenthaler, W. Lukosz, "Sensitivity of grating couplers as integrated-optical chemical sensors", J. Opt. Soc. Am. B6, 209 (1989); W. Lukosz, Ph. M. Nellen, Ch. Stamm, P. Weiss, "Output Grating Couplers on Planar Waveguides as Integrated, Optical Chemical Sensors", Sensors and Actuators B1, 585 (1990); and in T. Tamir, S. T. Peng, "Analysis and Design of Grating Couplers", Appl. Phys. 14, 235-254 (1977).

In U.S. Pat. No. 5,738,825, an arrangement consisting of a microtiter plate with bores extending all through the plate, and of a thin-film waveguide as the base plate is disclosed, the latter thin-film waveguide consisting of a thin waveguiding film on a transparent, self-supporting substrate. Diffraction gratings for the in- and outcoupling of excitation light are provided in contact with the open sample compartments formed by the perforated microtiter plate and the thin-film waveguide as the base plate, in order to determine changes of the effective refractive index, due to adsorption or desorption of analyte molecules to be determined, from the resulting changes of the observed coupling angles. A determination of multiple analytes in one sample compartment, upon binding recognition elements in the sample compartment on the grating structure, is not attended and appears hardly practicable because of the refractive measurement principle, i.e., the determination of relative changes of the coupling angle.

The aforesaid refractive methods have the advantage that they can be applied without using additional marker molecules, so-called molecular labels. The disadvantage of these label-free methods, however, is that the achievable detection limits are limited to pico- to nanomolar concentration ranges dependent on the molecular weight of the analyte due to lower selectivity of the measurement principle, which is not sufficient for many applications of modern trace analysis, for example, for diagnostic applications.

For achieving lower detection limits, luminescence-based methods appear as more adequate because of higher selectivity of signal generation. In this arrangement, luminescence excitation is limited to the penetration depth of the evanescent field into the medium of lower refractive index, i.e., to immediate proximity of the waveguiding area, with a penetration depth of the order of some hundred nanometers into the medium. This principle is called evanescent luminescence excitation.

By means of highly refractive thin-film waveguides, based on only some hundred nanometers thin waveguiding film on a transparent support material, the sensitivity could be increased considerably during the last years. In WO 95/33197, for example, a method is described, wherein the excitation light is coupled into the waveguiding film by a relief grating as a diffractive optical element. The surface of the sensor platform is contacted with a sample containing the analyte, and the isotropically emitted luminescence from substances capable of luminescence that are located within the penetration depth of the evanescent field is measured by adequate measurement arrangements, such as photodiodes, photomultipliers or CCD cameras. The portion of evanescently excited radiation that has backcoupled into the waveguide can also be outcoupled by a diffractive optical element, like a grating, and be measured. This method is described in, for example, WO 95/33198.

A disadvantage of all methods for the detection of evanescently excited luminescence described as state of the art, especially in WO 95/33197 and WO 95/33198, is that always only one sample can be analyzed on the waveguiding layer of the sensor platform, which layer is formed as a homogeneous film. In order to perform further measurements on the same sensor platform, tedious washing or cleaning steps are continuously required. This especially holds if an analyte different from the one in the first measurement has to be determined. In the case of an immunoassay, this means, in general, that the whole immobilized layer on the sensor platform has to be exchanged, or that even a whole new sensor platform has to be used.

For example, in WO 96/35940, arrangements (arrays) have been proposed, wherein at least two discrete waveguiding areas to which excitation light is launched separately are provided on one sensor platform, in order to perform exclusively luminescence-based, multiple measurements with essentially monomodal, planar anorganic waveguides simultaneously or sequentially. A drawback resulting from the partitioning of the sensor platform into discrete waveguiding areas, however, is the relatively large need of space for discrete measurement areas in discrete waveguiding regions on the common sensor platform, because of which again only a relatively low density of different measurement areas (or so-called "features") can be achieved.

In the spirit of this invention, spatially separated measurement areas (d) shall be defined by the area that is occupied by biological, biochemical or synthetic recognition elements immobilized thereon for recognition of one or multiple analytes in a liquid sample. These areas can have any geometry, for example, in the form of dots, circles, rectangles, triangles, ellipses or lines.

Besides numerous other arrangements for the design of sample compartments for measurement arrangements for the determination of luminescence excited in the evanescent field of a planar waveguide, in WO 98/22799, arrangements with the shape of known microtiter plates are proposed. The determination of multiple analytes upon their binding to different recognition elements immobilized within a single sample compartment, however, is also in this disclosure not been taken care of.

Therefore, there is a need for providing small-volume sample compartments combined with adequate sensor platforms, wherein a multitude of analytes can be determined simultaneously without great effort in a highly sensitive analysis method.

Surprisingly, it now has been found that significantly lower detection limits and higher integration density of measurement areas can be achieved in comparison to the known classical arrangements and methods (such as ELISA tests on classical microtiter plates), upon the chosen combination of highly efficient fluorescence excitation in the evanescent field of an adequate waveguide, especially of thin-film waveguides, with an arrangement of multiple measurement areas with different biological or biochemical recognition elements in a single sample compartment, as part of a two-dimensional array of sample compartments on a common sensor platform. Thereby, the analyte determination by luminescence during the detection step of a given assay can be performed upon addition of luminescently labeled binding partners for the actual bioaffinity assay without an additional washing step, which is a simplification of the assay.

Surprisingly, statistically relevant information, for example, concerning the assay reproducibility, can already be generated in a single measurement upon the arrangement of multiple measurement areas and different biological or biochemical recognition elements in a single sample compartment, after addition of a single sample. The data generated thereby are even characterized by a lower variability than the results of a corresponding number of single measurements in discrete sample compartments, because numerous potential additional sources for variabilities and errors of the measurements independent from each other can be excluded in the simultaneous measurement. Thus, a significant reduction of analysis time and of required amounts of samples and reagents can be achieved, in comparison with the known analysis methods (such as ELISA) described above. Referencing measurements, especially for the determination of chemical parameters, such as non-specific binding, cross reactivities, determination of pH or $pO_2$ of the sample solution, etc., can be performed in every single sample compartment upon providing one or more measurement areas in a sample compartment for such referencing measurements. Thus, the reliability of these referencing measurements can be improved significantly in comparison with the conventional methods, where these measurements are performed in different sample compartments.

With the device and the analysis method performed with the device, the number of measurements per plate and the through-put can be increased many times. Thus, the reproducibility of the measurements and the comparability of the results with different samples can be improved significantly, besides others due to the elimination of the typical large variations from plate to plate. For example, with 96 sample compartments, each comprising 400 measurement areas, on a single sensor platform, comprehensive measurement series, for example, for pharmaceutical product development typically requiring 400 microtiter plates can be performed on a single sensor platform. In addition to the significant reduction of sample and reagent amounts and an associated reduced effort for sample preparation, the reliability and precision of the results is significantly improved because of the above-mentioned reasons.

Thus, the device and the method according to the invention offer capabilities, which cannot be provided by the conventional, known analysis systems and method, such as: Fast assay development on a single sensor platform/device; Determination of dose-response curves, cross-talk and analysis of an unknown sample on a single sensor platform/device;

Highly sensitive multi-analyte determination in a single, small-volume sample; and Execution of comprehensive measurement series on a single sensor platform.

Figure 1:
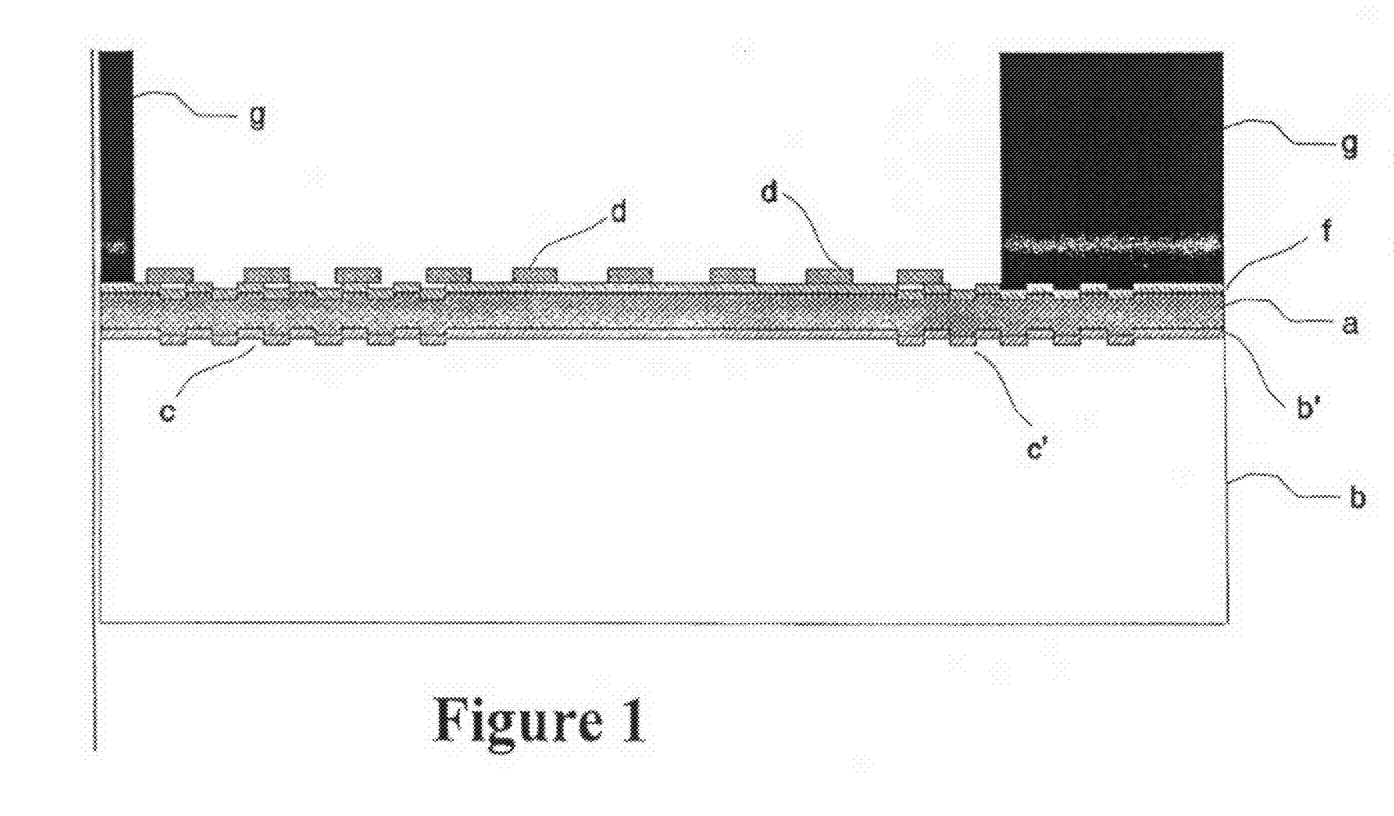
FIG. 1 is a planar optical wave-guide comprising a first optically transparent layer (a) on a second optically transparent layer (b) with lower refractive index than layer (a). The FIGURE further shows a layer (g) which is in contact with the sensor platform. Further, the FIGURE shows an adhesion promoting layer (f) for mobilization of biological, biochemical or synthetic recognition elements. Finally, the FIGURE shows laterally separated measurement areas (d).

An object of the invention is a device comprising a planar optical waveguide, as part of a sensor platform, and, connected to the platform directly or by means of a sealing medium, a layer (g) (according to FIG. 1), the layer forming either directly a tight seal or by means of the sealing medium, a tightly sealing layer. The device also comprises a multitude of recesses at least open towards the sensor platform, which form a corresponding multitude of sample compartments in a 2-dimensional arrangement, wherein in each of the sample compartments different biological or biochemical recognition elements, for the specific recognition and binding of different analytes, are immobilized in five or more discrete measurement areas (d) (according to FIG. 1) in these sample compartments, wherein the measurement areas are in optical interaction with the excitation light emanating from the optical waveguide, as part of a sensor platform which forms a demarcation surface of the sample compartments, and wherein the sample compartments are operable to be cleared of the received sample or reagent solutions and to receive, in the following, optionally without washing steps, a further sample or reagent solutions, which are supplied to the same sample compartments.

One or more measurement areas in each of the sample compartments, out of the five or more measurement areas in a single sample compartment, can be used for referencing.

It is advantageous if measurement areas for referencing the same chemical or optical parameters are used in several sample compartments distributed over the sensor platform, so that the lateral distribution of the chemical or optical parameters over the sensor platform can be determined. For example, the intensity of the available excitation light has to be understood as an optical parameter to be determined. From the distribution of chemical parameters thus determined, especially differences of composition, concentration, or volume of different samples, for example, resulting from the sample preparation, the samples being added to different sample compartments can be taken into account.

An embodiment of the device is preferred, wherein the measurement areas are in optical interaction with the evanescent field of excitation light guided in the planar optical waveguide.

The optical waveguide, as part of the sensor platform, can be a multi-mode or single-mode waveguide comprising an inorganic material, preferably glass, or an organic material, preferably a plastic, which is preferably selected from the group comprising polymethylmethacrylate, polycarbonate or polystyrene, which materials are optically transparent at least at the excitation and a luminescence wavelength. In this case, the optical waveguide, as a part of the sensor platform, can be self-supporting.

Preferred is a device, wherein the optical film waveguide, as part of the sensor platform, is an optical film waveguide with a first optically transparent layer (a) (according to FIG. 1) on a second optically transparent layer (b) (according to FIG. 1) with lower refractive index than layer (a).

The material of the second optically transparent layer (b) can comprise glass, quartz, or transparent thermoplastic plastics, preferably of the group comprising polycarbonate, polyimide, polymethylmethacrylate, or polystyrene.

For generation of an evanescent field as strong as possible on the surface of the optically transparent layer (a), it is desirable that the refractive index of the waveguiding, optically transparent layer (a) is significantly higher than the refractive index of the adjacent layers. It is especially of advantage if the refractive index of the first optically transparent layer (a) is higher than 1.8.

For example, the first optically transparent layer (a) can comprise $TiO_2$, $ZnO$, $Nb_2O_5$, $Ta_2O_5$, $HfO_2$, or $ZrO_2$. It is especially preferred, if the first optically transparent layer (a) comprises $Ta_2O_5$ or $Nb_2O_5$.

Besides the refractive index of the waveguiding, optically transparent layer (a), its thickness is the second controlling parameter for the generation of an evanescent field as strong as possible at the interfaces between layer (a) and the adjacent layers with lower refractive index. With decreasing thickness of the waveguiding layer (a), the strength of the evanescent field increases, as long as the layer thickness is sufficient for guiding at least one mode of the excitation wavelength. Thereby, the minimum "cut-off" layer thickness for guiding a mode is dependent on the wavelength of this mode. The "cut-off" layer thickness is larger for light of longer wavelength than for light of shorter wavelength. In approaching the "cut-off" layer thickness, however, unwanted propagation losses also increase strongly, thus setting additionally a lower limit for the choice of the preferred layer thickness. Preferred are layer thicknesses of the optically transparent layer (a) allowing for guiding only one to three modes at a given excitation wavelength. Especially preferred are layer thicknesses resulting in monomodal waveguides for this given excitation wavelength. It is understood that the character of discrete modes of the guided light only refers to the transversal modes.

Resulting from these requirements, the thickness of the first optically transparent layer (a) is preferably between 40 and 300 nm. It is especially advantageous, if the thickness of the first optically transparent layer (a) is between 100 and 200 nm.

The amount of the propagation losses of a mode guided in an optically waveguiding layer (a) is determined to a large extent by the surface roughness of a supporting layer below and by the absorption of chromophores which might be contained in this supporting layer, which is additionally associated with the risk of excitation of unwanted luminescence in this supporting layer upon penetration of the evanescent field of the mode guided in layer (a) (into this supporting layer). Furtheron, thermal stress can occur due to different thermal expansion coefficients of the optically transparent layers (a) and (b). In case of a chemically sensitive optically transparent layer (b), consisting, for example, of transparent thermoplastic plastics, it is desirable to prevent a penetration, for example, through micro pores in the optically transparent layer (a), of solvents that might attack layer (b).

Therefore, it is advantageous, if an additional optically transparent layer (b') (according to FIG. 1) with lower refractive index than and in contact with layer (a), and with a thickness of 5 nm-10 000 nm, preferably of 10 nm-1000 nm, is located between the optically transparent layers (a) and (b). The purpose of the intermediate layer is a reduction of the surface roughness below layer (a), a reduction of the penetration of the evanescent field, of light guided in layer (a), into the one or more layers located below, an improvement of the adhesion of layer (a) to the one or more layers located below or a reduction of thermally induced stress within the optical sensor platform or a chemical isolation of the optically transparent layer (a) from layers located below, by sealing of micropores in layer (a) against the layers located below.

There are many methods for the deposition of the biological, biochemical or synthetic recognition elements on the optically transparent layer (a). For example, the deposition can be performed by physical adsorption or electrostatic interaction. In general, the orientation of the recognition elements is then of statistic nature. Additionally, there is the risk of washing away a part of the immobilized recognition elements, if the sample containing the analyte and reagents applied in the analysis process have a different composition. Therefore, it can be advantageous, if an adhesion-promoting layer (f) (according to FIG. 1) is deposited on the optically transparent layer (a), for immobilization of biological, biochemical or synthetic recognition elements. This adhesion-promoting layer should be transparent as well. It is noted that the thickness of the adhesion-promoting layer should not exceed the penetration depth of the evanescent field out of the waveguiding layer (a) into the medium located above. Therefore, the adhesion-promoting layer (a) should have a thickness of less than 200 nm, preferably of less than 20 nm. The adhesion-promoting layer can comprise, for example, chemical compounds of the group comprising silanes, epoxides, and "self-organized functionalized monolayers".

As stated in the definition of the measurement areas, laterally separated measurement areas (d) can be generated by laterally selective deposition of biological, biochemical or synthetic recognition elements on the sensor platform. When brought into contact with an analyte capable of luminescence, with a luminescently marked analogue of the analyte competing with the analyte for the binding to the immobilized recognition elements or with a luminescently marked binding partner in a multi-step assay, these molecules capable of luminescence will bind to the surface of the sensor platform selectively only in the measurement areas, which are defined by the areas occupied by the immobilized recognition elements.

For the deposition of the biological, biochemical or synthetic recognition elements, one or more methods of the group of methods comprising ink jet spotting, mechanical spotting by pin or pen, micro contact printing, fluidic contacting of the measurement areas with the biological, biochemical or synthetic recognition elements upon their supply in parallel or crossed micro channels, upon application of pressure differences or of electric or electromagnetic potentials, can be applied.

Components of the group comprising nucleic acids (DNA, RNA), nucleic acid analogues (peptide nucleic acids, PNA), antibodies, aptamers, membrane-bound and isolated receptors, their ligands, antigens for antibodies, "histidin-tag components", cavities generated by chemical synthesis, for hosting molecular imprints, etc., can be deposited as biological, biochemical or synthetic recognition elements.

With the last-named type of recognition elements are meant cavities that are produced by a method described in the literature as "molecular imprinting". In this procedure, the analyte or an analyte-analogue, mostly in organic solution, is encapsulated in a polymeric structure. Then it is called an "imprint". Then the analyte or its analogue is dissolved from the polymeric structure upon addition of adequate reagents, leaving an empty cavity in the polymeric structure. This empty cavity can then be used as a binding site with high steric selectivity in a later process of analyte determination.

Also whole, cells or cell fragments can be deposited as biological or biochemical recognition elements.

In many cases, the detection limit of an analytical method by signals is caused by so-called nonspecific binding, i.e., by signals caused by the binding of the analyte or of other components applied for analyte determination, which are not only bound in the area of the provided immobilized biological, biochemical or synthetic recognition elements, but also in areas of a sensor platform that are not occupied by these recognition elements, for example, upon hydrophobic adsorption or electrostatic interactions. Therefore, it is advantageous if compounds that are "chemically neutral" towards the analyte are deposited between the laterally separated measurement areas (d), in order to reduce nonspecific binding or adsorption. As "chemically neutral" compounds such components are called, which themselves do not have specific binding sites for the recognition and binding of the analyte, of an analogue of the analyte or of a further binding partner in a multistep assay and which prevent, due to their presence, the access of the analyte, of its analogue or of the further binding partners to the surface of the sensor platform.

Compounds of the groups comprising, for example, albumines, especially bovine serum albumine, herring sperm or also polyethyleneglycols, can be applied as "chemically neutral" compounds.

It is preferred, that the incoupling of excitation light to the measurement areas (d) is performed by means of one or more grating structures (c) (according to FIG. 1), which are formed in the optically transparent layer (a).

An optical cross-talk from one measurement area to other measurement areas can occur upon the spreading of light incoupled into the waveguide, especially of backcoupled luminescence light. For the prevention of such a cross-talk, it is advantageous if outcoupling of light guided in the optically transparent layer (a) is performed by means of grating structures (c') (according to FIG. 1), which are formed in the optically transparent layer (a). Thereby, grating structures (c) and (c') formed in the optically transparent layer (a) can have the same or different periodicity and can be arranged in parallel or not in parallel to each other.

It is especially noted that, grating structures (c) and (c') can be used interchangeably as incoupling and/or outcoupling gratings.

It is of advantage if the grating structures (c) and optional additional grating structures (c') have a period of 200 nm-1000 nm and a grating modulation depth of 3 nm-100 nm, preferably of 10 nm-30 nm.

It is preferred that the ratio of the modulation depth to the thickness of the first optically transparent layer (a) is equal or smaller than 0.2.

A grating structure (c) can be a relief grating with rightangular, triangular or semi-circular profile or a phase or volume grating with a periodic modulation of the refractive index in the essentially planar optically transparent layer (a).

For the enhancement of a luminescence or for the improvement of the signal-to-noise ratio, it can additionally be advantageous if a thin metal layer, preferably of gold or silver, optionally on an additional dielectric layer of lower refractive index than layer (a), for example, of silica or magnesium fluoride, is deposited between the optically transparent layer (a) and the immobilized biological or biochemical recognition elements, wherein the thickness of the metal layer and the optional, additional intermediate layer is selected in such a way that a surface plasmon at the excitation wavelength and/or at the luminescence wavelength can be excited.

For many applications it is advantageous, if the grating structure (c) is a diffractive grating with a uniform period. Then, the resonance angle for incoupling of the excitation light by the grating structure (c) towards the measurement areas is uniform in the whole area of the grating structure. If it is intended, however, to incouple excitation light from different light sources of significantly different wavelength, the corresponding resonance angles for the incoupling can differ considerably, which can lead to the need for additional components for adjustment in an optical system housing the sensor platform or to spatially very unfavorable coupling angles. For example, for reducing large differences of coupling angles, it can be advantageous if the grating structure (c) is a multidiffractive grating.

For applications where changes of in- and outcoupling angles due to contacts with the sample shall be avoided, it can be advantageous if grating structures (c) and optional additional grating structures (c') are located outside the region of the sample compartments.

For other applications, especially for large-area excitation, on the other side, it is preferred that grating structures (c) and optional additional grating structures (c') extend over the range of multiple or all sample compartments.

If excitation light incoupled by a grating structure (c) shall propagate in the optically transparent layer (a) over ranges extending over multiple sample compartments, it is required that the material of the tightly sealing layer (g) in contact with the sensor platform, in the incumbent surface area, is optically transparent both for the excitation radiation and the excited luminescence radiation at least within the penetration depth of the evanescent field.

Then, it is advantageous for a reduction of reflections or of scattered light that the layer (g) is provided in form of a two-layer system, the first layer of which, to be brought into contact with the surface of the sensor platform, being transparent for the excitation radiation and the excited luminescence radiation, whereas the adjacent layer, being located more remote from the sensor platform, is absorbent in the spectral range of the excitation radiation and of the excited luminescence radiation.

On the other side, for applications, where the propagation of excitation light and optionally generated luminescence light backcoupled into the optically transparent, waveguiding layer (a) shall be limited in the layer (a) to the range of a single sample compartment, it is advantageous if the material of the tightly sealing layer (g) in contact with the sensor platform is absorbent in the spectral range of the excitation radiation and of the excited luminescence radiation.

It is advantageous if the material of the tightly sealing layer (g) in contact with the sensor platform is self-adhesive.

Therefore, it is especially preferred that the material of the tightly sealing layer (g) in contact with the sensor platform comprises a poly siloxane.

It is preferred that 5-1000, preferably 10-400, measurement areas are located in one sample compartment.

Furtheron, it is preferred that an individual measurement area in a sample compartment occupies an area of 0.001-6 $mm^2$, wherein the measurement areas can have similar or different size.

Preferably, the sample compartments have a volume of 100 nl-1 ml each.

The device according to the invention can be operated both as a closed flow system and as an open system. In the first case, the device is designed in such a way that, at the side facing away from the optically transparent layer (a), the sample compartments are closed except for inlet and outlet openings for the supply or removal of samples and optional additional reagents, wherein the supply or removal of samples and optional additional reagents is performed in a closed flow-through system, and wherein in the case of liquid supply to measurement areas or segments with common inlet and outlet openings, the inlet and outlet openings are preferably addressed row by row or column by column.

Thereby, the supply of samples and optional additional reagents is performed in parallel or crossed micro channels affected by pressure differences or by electric or electromagnetic potentials.

In case of an open system, the device according to the invention is designed in such a way that the sample compartments have openings for the locally addressed supply or removal of samples or other reagents at the side facing away from the optically transparent layer (a). Additionally, compartments may be provided for reagents, which are wetted and brought into contact with the measurement areas during the assay.

It is advantageous if optically or mechanically recognizable marks are provided on the sensor platform in order to facilitate the adjustment in an optical system and/or to facilitate the combination of the sensor platform with the layer (g) comprising the recesses for the sample compartments.

A further subject of the invention is an analytical system for the determination of one or more luminescences, comprising: at least one excitation light source; a device according to one of the embodiments disclosed above; and at least one detector for recording the light emanating from the at least one or more measurement areas (d) on the sensor platform.

Thereby, it is advantageous if the excitation light emitted by the at least one light source is coherent and directed onto the one or more measurement areas at the resonance angle for incoupling into the optically transparent layer (a).

In order to excite a multitude of measurement areas or all measurement areas simultaneously, it is preferred that the excitation light of at least one light source is expanded to an essentially parallel ray bundle by expansion optics and directed onto the one or more measurement areas at the resonance angle for incoupling into the optically transparent layer (a).

For a reduction of luminescence signals outside of the measurement areas, however, it can also be advantageous if the excitation light from at least one light source is divided, by means of one or, in case of several light sources, by means of multiple diffractive optical elements, preferably Dammann gratings, or refractive optical elements, preferably micro-lens arrays, into a multitude of individual beams, with as similar an intensity as possible of the individual beams originating from a common light source, which individual beams are directed essentially in parallel to each other onto laterally separated measurement areas.

In case of insufficient intensity of a single light source or of the need for light sources of different emission wavelengths, for example, for biological applications, it is advantageous if two or more coherent light sources with equal or different emission wavelength are used as excitation light sources.

In order to record signals from a multitude of measurement areas separately, it is preferred that at least one laterally resolving detector is used for detection. Thereby, at least one detector from the group formed by CCD cameras, CCD chips, photodiode arrays, Avalanche diode arrays, multi-channel plates, and multi-channel photomultipliers may be used as at least one laterally resolving detector.

In the analytical system according to the invention, according to any of the embodiments disclosed above, optical components of the group comprising lenses or lens systems for the shaping of the transmitted light bundles, planar or curved mirrors for the deviation and optionally additional shaping of the light bundles, prisms for the deviation and optionally spectral separation of the light bundles, dichroic mirrors for the spectrally selective deviation of parts of the light bundles, neutral density filters for the regulation of the transmitted light intensity, optical filters or monochromators for the spectrally selective transmission of parts of the light bundles, or polarization selective elements for the selection of discrete polarization directions of the excitation or luminescence light are located between the one or more excitation light sources and the sensor platform and/or between the sensor platform and the one or more detectors.

For many applications, it is advantageous if the excitation light is launched in pulses with duration of 1 fsec to 10 min.

For kinetic measurements, or for the discrimination of fast decaying fluorescence from fluorescent contaminations in the sample or in materials of components of the analytical system or of the sensor platform itself, it can be advantageous if the emission light from the measurement areas is measured time-resolved.

It is further preferred that the analytical system according to the invention comprises components dedicated for measuring, for referencing purposes, light signals of the group comprising excitation light at the location of the light sources, after expansion of the excitation light or after its multiplexing into individual beams, scattered light at the excitation wavelength from the location of the one or more laterally separated measurement areas, and light of the excitation wavelength outcoupled by the grating structures (c) or (c'). Thereby, it is of special advantage if the measurement areas for determination of the emission light and of the reference signal are identical.

Launching of the excitation light and detection of the emission light from the one or more measurement areas can also be performed sequentially for one or more sample compartments. Thereby, sequential excitation and detection can be performed using movable optical components of the group comprising mirrors, deviating prisms, and dichroic mirrors. Typically, commercially available so-called scanners are used for sequential excitation and detection for bioanalytical array systems, wherein an excitation light beam is scanned sequentially over the area to be investigated, usually by means of movable mirrors. Thereby, in case of most scanner systems, the angle between the illuminated surface and the excitation light beam is changed. For satisfying the resonance condition for the incoupling of the excitation light into the waveguiding layer of the sensor platform according to the invention, however, this angle should essentially remain constant, i.e., a scanner to be implemented in the optical system according to the invention has to function in an angle-preserving manner. This requirement is satisfied by some commercially available scanners. At the same time, however, the size of the excited area on the sensor platform should also not be changed.

Therefore, another subject of the invention is an optical system, wherein sequential excitation and detection is performed using an essentially focus and angle preserving scanner.

In another embodiment, the sensor platform is moved between steps of sequential excitation and detection. In this case, the one or more excitation light sources and the components used for detection can be located at spatially fixed positions.

A further object of the invention is a method for determination of one or more analytes by luminescence in one or more samples on at least five, laterally separated measurement areas, with a device comprising a planar optical waveguide as part of a sensor platform, and, connected to the platform directly or by means of a sealing medium, a layer (g), the layer forming either a tight seal directly or by means of the sealing medium a tightly sealing layer. The device also comprises a multitude of recesses at least open towards the sensor platform, which form a corresponding multitude of sample compartments in a 2-dimensional arrangement, wherein in each of the sample compartments different biological or biochemical recognition elements, for the specific recognition and binding of different analytes, are immobilized in five or more discrete measurement areas (d) in these sample compartments, wherein the measurement areas are in optical interaction with the excitation light emanating from the optical waveguide, as part of a sensor platform which forms a demarcation of the sample compartments, wherein the sample compartments are operable to be cleared from received sample or reagent solutions and to receive, in the following, optionally without washing steps, a further sample or reagent solutions, which are supplied to the same sample compartments, wherein excitation light is directed to the measurement areas, leading to excite substances capable of luminescence in the samples or on the measurement areas to emit luminescence, and wherein the emanated luminescence is measured.

Thereby, it is preferred that the measurement areas are in optical interaction with the evanescent field of excitation light guided in the planar optical waveguide.

In the method disclosed above, (1) the isotropically emitted luminescence or (2) luminescence that is incoupled into the optically transparent layer (a) and outcoupled by a grating structure (c) or luminescence comprising both parts (1) and (2) can be measured simultaneously.

For the generation of the luminescence or fluorescence in the method according to the invention, a luminescence or fluorescence label can be used that can be excited and emits at a wavelength between 300 nm and 1100 nm.

The luminescence or fluorescence labels can be conventional luminescence or fluorescence dyes or also so-called luminescent or fluorescent nano-particles based on semiconductors (W. C. W. Chan and S. Nie, "Quantum dot biocomjugates for ultrasensitive nonisotopic detection", *Science* 281 (1998) 2016-2018).

The luminescence label can be bound to the analyte or, in a competitive assay, to an analyte analogue or, in a multi-step assay, to one of the binding partners of the immobilized biological, biochemical or synthetic recognition elements or to the biological, biochemical or synthetic recognition elements.

Additionally, a second or more luminescence labels of similar or different excitation wavelength as the first luminescence label and similar or different emission wavelength can be used. Thereby, it can be advantageous if the second or more luminescence labels can be excited at the same wavelength as the first luminescence label, but emit at other wavelengths.

For other applications, it is advantageous if the excitation and emission spectra of the applied luminescent dyes do not overlap or overlap only partially.

In the method according to the invention, it can also be advantageous if charge or optical energy transfer from a first luminescent dye acting as a donor to a second luminescent dye acting as an acceptor is used for the detection of the analyte.

In addition, it can be of advantage if besides determination of one or more luminescences, changes of the effective refractive index on the measurement areas are determined. It can be of further advantage if the one or more luminescences and/or determinations of light signals at the excitation wavelengths are performed polarization-selective. The method also allows for measuring the one or more luminescences at a polarization that is different from the one of the excitation light.

The method according to the invention, according to any of the embodiments disclosed above, allows for the simultaneous or sequential, quantitative or qualitative determination of one or more analytes of the group comprising antibodies or antigens, receptors or ligands, chelators or "histidin-tag components", oligonucleotides, DNA or RNA strands, DNA or RNA analogues, enzymes, enzyme cofactors or inhibitors, lectins and carbohydrates.

The method disclosed above allows for determining biological material directly, without biological or biochemical multiplication mechanisms (such as polymerase chain reaction, PCR). Besides a simplification of the approach, here a linear correlation between mRNA and the observed signal is achieved; i.e., aksi so-called "rare messages" (biologically relevant mRNA's occurring at very low concentrations) can be determined quantitatively and with high sensitivity. The parallel execution of the measurements on a 96-well plate platform allows for obtaining results of unpreceded quality and through-put (see Example 1(e)). As a consequence, the large numbers of samples generated by pre-clinical and clinical studies can be analyzed much faster and more precisely than with current manual methods.

In addition, the detection of two fluorescence markers on one substance spot allows for the direct determination of the relative induction in a single Experiment (see Example 2(e)). Therefore, a referencing from chip-to-chip is not required. Therefore, the quality requirements on batch-to-batch reproducibility of the sensor platforms can be lowered significantly.

The samples to be examined can be naturally occurring body fluids, such as blood, serum, plasma, lymphe or urine, or egg yolk.

A sample to be examined can also be an optically turbid liquid or surface water or soil or plant extract or bio- or process broths.

The samples to be examined can also be taken from biological tissue.

A further object of the invention is the use of a method according to any of the above embodiments for the quantitative or qualitative determination of chemical, biochemical or biological analytes in screening methods in pharmaceutical research, combinatorial chemistry, clinical and preclinical development, for real-time binding studies and the determination of kinetic parameters in affinity screening and in research, for qualitative and quantitative analyte determinations, especially for DNA- and RNA analytics and for the determination of genomic or proteomic differences in the genome, such as single nucleotide polymorphisms, for the measurement of protein-DNA interactions, for the determination of control mechanisms for mRNA expression and for the protein (bio)synthesis, for the generation of toxicity studies and the determination of expression profiles, especially for the determination of biological and chemical marker compounds, such as mRNA, proteins, peptides or small-molecular organic (messenger) compounds, and for the determination of antibodies, antigens, pathogens or bacteria in pharmaceutical product development and research, human and veterinary diagnostics, agrochemical product development and research, for symptomatic and pre-symptomatic plant diagnostics, for patient stratification in pharmaceutical product development and for the therapeutic drug selection, for the determination of pathogens, nocuous agents and germs, especially of salmonella, prions and bacteria, in food and environmental analytics.

The invention will be explained and demonstrated by the following examples.

Example 1

Device and Method for the Simultaneous Determination of Differences in the Expression Pattern of Selected mRNA's from Different Locations in Tumor Tissue Tissue is taken from different sites on an isolated tumor—in this case of a prostate gland—and examined for differences in the expression pattern of selected mRNAs as a function of the site in the tumor tissue. The results will allow for conclusions based on exclusively genetic informations, independent from histologic examinations. The biological relevance of such a method and aspects of the sample preparation are described in the literature (Kristina A. Cole, David B. Krizmann, and Michael R. Emmert-Buck, "The genetics of cancer—a 3D model", *Nature Genetics Supplement* 21 (1999) 38-41).

Preparation and Deposition of the Biological Recognition Elements on a Sensor Platform of a Device with 400 Discrete Measurement Areas in Each of its 96 Sample Compartments (a) Clones of 100 genes relevant in carcinogenesis or in inflammatory reactions—according to results described in the literature (see Kristina A. Cole, David B. Krizmann, and Michael R. Emmert-Buck, "The genetics of cancer—a 3D model", *Nature Genetics Supplement* 21 (1999) 38-41, and the references cited therein)—and of such genes, which are typically not involved in these reactions, but show a constant expression level, in the ideal case, and can, therefore, be utilized for standardization (so-called "house-keeping genes", such as β-actin, GAPDH, tubulin-α, ubiquitin, phospholipase A2, etc.) are selected as biological recognition elements to be immobilized in discrete measurement areas on the sensor platform.

Besides others, the first group of genes potentially relevant for diseases comprises serin/threonin kinase (STK2), the beta-subunit of proteasom (PSMB4), CD36-antigen (Collagen type I receptor, thrombospondin receptor), phospholipase A2 (PLA2G1B), ribosomal protein L17 (RPL17), desmoglein 2 (DSG2), tyro 3 protein-tyrosin kinase (TYRO3), type IV collagen (COL4A4), "activating transcription factor 3" (ATF3), annexin 1 (ANX), further repair enzymes, kinases, etc.

The required genetic material can be obtained in plasmid form from UniGene SET NIH Cancer Genome Anatomy Projects or, alternatively, from commercial providers distributing the material of the I.M.A.G.E. association. The transfer and amplification of the gene sequences in the plasmid to generate the corresponding cDNAs is performed by means of the corresponding primer pairs and leads to double-stranded molecules (probe cDNAs) with a length between about 300 and 1000 base pairs.

(b) A sensor platform with the exterior dimensions of 76 mm width×112 mm length×0.7 mm thickness is used. On the surface of the sensor platform, 96 wells with inside dimensions of 7 mm×7 mm of a classical microtiter plate can be arranged. The substrate material (optically transparent layer (b)) consists of AF 45 glass (refractive index n=1.52 at 633 nm). A continuous structure of a surface relief grating with a period of 360 nm and a grating depth of 25+/−5 nm and with an orientation of the grating lines in parallel to the width of the sensor platform as defined above, is generated in the substrate. The waveguiding, optically transparent layer (a) of $Ta_2O_5$ on the optically transparent layer (b) has a refractive index of 2.15 at 633 nm (layer thickness 150 nm). Due to the deposition process, the grating structure is transferred into the surface of the waveguiding layer almost 1:1 according to scale.

As a preparation for the immobilization of the biochemical or biological or synthetic recognition elements, the sensor platforms are cleaned with chloroform in an ultrasonic apparatus, chemically activated by a silanization reaction with glycidyloxypropyltrimethoxy silane, and thus prepared for the immobilization of the probe cDNAs as biological recognition elements. The individual cDNAs, at a concentration of 50 ng/µl, are deposited as spots of 10 drops (0.1 nl) each, using a commercial, piezo-controlled micropipette (GeSIM, Großerkmannsdorf, DE), resulting in spots as discrete measurement areas of about 150 µm. In a 20×20 spot arrangement (array of 400 features), always 4 measurement areas with the same cDNA are provided in a way that, at the end of the immobilization step, the position of the 100 different cDNAs as recognition elements, defined by a statistic algorithm, is known, but pre-determined in a purely statistical way. The distance between the spot centers is 300 µM, and the spots cover an area of 6 mm×6 mm on the sensor platform, forming, together with a tightly sealing layer (g) of polydimethylsiloxane (PDMS) with square recesses of 7 mm×7 mm surrounding the arrays, a 96-well plate. At the bottom of every 96 sample compartments, an identical pattern of discrete measurement areas is generated on the sensor platform. The immobilization can be optimized by thermal treatment, i.e. heating up to 60° C. for 30 min.

(c) Sample Material

Tissue material (about 50,000 to 100,00 cells) is taken, for example, as fine tissue slices, from different sites of a prostate gland (both in the phenomenologically normal and malignant tissue. The tissue is dissected in the frozen state, and "total RNA" is extracted by a standard phenol/chloroform extraction. mRNA is isolated from the total RNA fraction using an Oligotex spin column (Qiagen, Hilden, Del.). All mRNA molecules are transferred into fluorescently labeled cDNA molecules in a reversed transcriptase process (e.g., Life Technologies) in the presence of a Cy5-labeled nucleobase (Cy5-dUTP; Pharmacia Amersham). The obtained material is dissolved in a hybridization buffer, thus obtaining a liquid sample with a total concentration of 10 ng/µl at maximum.

(d) Analytical System

Optical System (i) Excitation Unit

The sensor platform is mounted on a computer-controlled adjustment module, allowing for translation in parallel and perpendicular to the grating lines and for rotation around an axis in parallel to the grating lines and with center of motion in the main axis of the area illuminated by the excitation light beam launched onto the grating structure (I) for incoupling into the sensor platform named in example 1b. Immediately after the laser acting as an excitation light source, there is a shutter in the light path in order to block the light path when measurement data is not to be collected. Additionally, neutral density filters or polarizers can be mounted at this or also other positions in the path of the excitation light towards the sensor platform in order to vary the excitation light intensity step-wise or continuously.

The excitation light beam from a helium neon laser, at 632.8 nm, is expanded to a parallel ray bundle of circular cross-section with 25 mm diameter by means of 25-fold expansion optics. From the central part of this excitation light bundle, a square area of 10 mm length×10 mm width (in accordance with the nomenclature for the grating structure) is selected and, after passing a dichroic mirror (650 DRLP, Omega Optical, Brattleborough, Vt., USA), directed through the optically transparent layer (a) onto one of the 96 arrays centered in the excitation light spot. The sensor platform is adjusted for maximum incoupling, which is confirmed by a minimum of the transmission of excitation light through the sensor platform and by a maximum of the sum of reflected excitation light and of excitation light outcoupled by the continuous grating structure (c), after incoupling under the same angle as the reflected light within the measurement precision. The optimum incoupling angle can be determined both by visual inspection and, under computer control, from the signals of photodiodes connected to amplifiers, which photodiodes are positioned in the related light paths. In this way, an angle of 3.5° is determined as the resonance angle for incoupling.

(ii) Detection

A CCD camera (TE3/A Astrocam, Cambridge, UK) with peltier cooling (operation temperature: −30° C.) is used as a laterally resolving detector. Signal collection and focusing onto the CCD chip is performed by means of a Heligon Tandem objective (Rodenstock, 2× Cine-Heligon 2.1/100 mm). The interference filters (Omega Optical, Brattleborough, Vt.), with central wavelength of 680 nm and 40 nm bandwidth, and either a neutral density filter (for transmission of attenuated, scattered excitation light and of much weaker luminescence light from the measurement areas) or a neutral density filter in combination with an interference filter (for transmission of the attenuated excitation light from the measurement areas) are mounted on a filter wheel between the two parts of the Heligon Tandem objective. The signals at the excitation and the emission wavelength are measured alternately. Data analysis is performed using commercially available image analysis software (ImagePro Plus).

(e) Method of Luminescence Detection of the Hybridization Reaction:

30 µl of the liquid samples prepared as described in section (c) "Sample Material" are filled, manually or using a laboratory robot (e.g., Beckman 2000), into each of the 96 sample compartments of the device disclosed above. Then, the sample compartments are hermetically sealed with a lid, leaving a steam space of 100 µl above each well.

In a first thermal step (temperature increase to 85° C. for 30 min), the double-stranded cDNAs immobilized on the surface are dehybridized (separated) and prepared for hybridization with the Cy5-labeled single-stranded cDNAs in the sample. Hybridization of immobilized single-stranded cDNA with complementary Cy5-labeled molecules is enabled under so-called stringent conditions (hybridization of only completely complementary single strands), upon slow cooling down to 43° C. (about 2° C. per minute) and then thermal equilibration at 43° C. for 8 hours. This situation can be stabilized by exchange of the residual sample liquid and upon lowering the temperature to ambient temperature.

For the (optical) read-out of the arrays in the individual sample compartments, the device described above is inserted into the disclosed analytical system and adjusted to maximum incoupling of excitation light in the array of the first of the 96 sample compartments, as described above, which is controlled at the position of the filter-wheel for transmission of the excitation wavelength. Then, the intensity of the fluorescence light from the measurement areas (spots) is measured with position of the filter-wheel for transmission at the luminescence wavelength. Read-it of the arrays in the other sample compartments is performed sequentially (always for one sample compartment after the other, with 400 measurement areas each), upon transfer of the device to the next position for read-out of the luminescence signals from the next sample compartment.

Example 2

Determination of the Type and Amount of Enzyme Induction in Toxicology and Drug Metabolism by a Fast and Highly Parallel, Differential Method of Measurement, Based on Micro Arrays In pharmaceutical product development, examinations of drug metabolism and toxicology studies are performed after application of xenobiotics (biologically and/or pharmaceutically active chemical substances) in experimental animals and humans. Besides others, the first metabolic degradation reactions in the liver, as the "First Path Metabolism" are investigated. After application of such substances, often an "enzyme induction", i.e., an affect on the concentration of the enzymes involved in the metabolism in the liver, typically from the group of the P450 iso-enzymes (mixed functional mono-oxygenases), is observed. This change then affects the quality and the rate of the further metabolizing of such substances. In the course of testing new pharmacologically active substances, it is necessary to measure these affects on the level of mRNA quantitatively and with high sensitivity, in comparison to the metabolism of untreated (not induced) organisms, at a very early phase of the test program.

Preparation and Deposition of the Biological Recognition Elements on a Sensor Platform of a Device with 400 Discrete Measurement Areas in Each of its 96 Sample Compartments (a) Clones of the 20 most important cytochrome P450 iso-enzymes described in the literature, which are involved in the "First Path Metabolism" in the liver, and 5 clones of genes typically not involved in these processes, the expression level of which remains constant, in the ideal case, and which can be utilized, therefore, for standardization (so-called "housekeeping genes", such as β-actin, GAPDH, tubulin-α, ubiquitin, phospholipase A2, etc.) are selected as biological recognition elements to be immobilized in discrete measurement areas on the sensor platform.

Besides others, the first group of selected biological marker substances comprises CYP1A1, CYP1A2, CYP2B1, CYP2B2, CYP3A1, CYP3A2, CYP4A1.

The required genetic material can be obtained commercially in plasmid form. The transfer and amplification of the gene sequences in the plasmid, to generate the corresponding cDNAs, is performed by means of the corresponding primer pairs and leads to double-stranded molecules (probe cDNAs) with a length between about 300 and 1000 base pairs.

(b) A sensor platform with the exterior dimensions of 76 mm width×112 mm length×0.7 mm thickness is used, on the surface of which 96 micro flow cells, with inside dimensions of 7 mm width×7 mm length×0.15 mm height, in the pitch (arrangement in rows and columns) of a classical microtiter plate can be arranged, by combining the sensor platform with a polycarbonate plate having open recesses facing the sensor platform. The recesses are tightly sealed against each other by means of sealing rings enclosing the recesses.

The substrate material (optically transparent layer (b)) consists of AF 45 glass (refractive index n=1.52 at 633 nm). A periodic sequence ("Raster") of pairs of in- and outcoupling gratings with grating lines (360 nm period) in parallel to the width of the sensor platform and with a grating depth of 12+/−3 nm is generated in the substrate, wherein the grating lines extend over the whole width of the sensor platform. The distance between subsequent grating pairs is 9 mm; and the length of the individual grating structures (in parallel to the length of the sensor platform) is 0.5 mm. The distance between the in- and outcoupling grating of a grating pair is 5.5 mm, allowing for in- and outcoupling of the excitation light always within the (inside) region of the sample compartments, after the combination of the sensor platform with the polycarbonate plate described above.

The waveguiding, optically transparent layer (a) of $Ta_2O_5$ on the optically transparent layer (b) has a refractive index of 2.15 at 633 nm (layer thickness 150 nm). Due to the deposition process, the grating structure is transferred into the surface of the waveguiding layer almost 1:1 according to scale.

The sample compartments formed by the combination of the sensor platform with the polycarbonate plate are provided with conically bored openings at the demarcation surface opposite to the sample compartments, thus allowing for a filling or clearing of the sample compartments by inserting standard-type, commercially available pipette tips of polypropylene.

As a preparation for the immobilization of the biochemical, biological or synthetic recognition elements, the sensor platforms are cleaned with chloroform in an ultrasonic apparatus, chemically activated by a silanization reaction with glycidyloxypropyltrimethoxy silane, and thus prepared for the immobilization of the probe cDNAs as biological recognition elements. The individual cDNAs, at a concentration of 50 ng/μl, are deposited as spots of 10 drops (0.1 nl) each, using a commercial, piezo-controlled micropipette (GeSIM, Großerkmannsdorf, DE), resulting in spots as discrete measurement areas of about 150 μm. In a 10×10 spot arrangement (array of 100 features), always 4 measurement areas with the same cDNA are provided in a way that, at the end of the immobilization step, the position of the 25 different cDNAs as recognition elements, defined by a statistic algorithm, is known, but pre-determined in a purely statistical way. The distance between the spot centers is 400 μm, and the spots cover an area of 4 mm×4 mm on the sensor platform. The immobilization can be optimized by thermal treatment, i.e., heating up to 60° C. for 30 min.

The described polycarbonate plate is combined with the prepared sensor platform in such a way, that the sample compartments are fluidically tightly sealed against each other by means of the enclosing seals and that the arrays of 100 measurement areas each, formed by the spots, are centered at the bottom of the sample compartments.

(c) Sample Material: (ii) mRNA from Non Induced Experimental Animals (Not Treated with Xenobiotics)

About 250 mg of liver from slayed mice are shock-frozen using liquid nitrogen, grinded in a mortar and degreased with chloroform. Then "total RNA" is isolated by a standard phenol/chloroform extraction. mRNA is isolated from the total RNA fraction, using an Oligotex spin column (Qiagen, Hilden, Del.). All mRNA molecules are transferred into fluorescently labeled cDNA molecules in a reversed transcriptase process (e.g., Life Technologies), in the presence of a Cy5-labeled nucleobase (Cy5-dUTP; Pharmacia Amersham). The obtained material is dissolved in hybridization buffer, thus obtaining a liquid sample with a total concentration of 10 ng/μl at maximum.

(ii) mRNA from Induced Experimental Animals (Treated with Xenobiotics, E.G., with Phenobarbital)

The preparation is performed in a way analoguous to Example 2(c)(i), with the only difference, that fluorescence labeling is performed using Cy3 (Amersham Pharmacia), instead of Cy5.

(iii) Labeled mRNA from the Preparations (i) and (ii) is Mixed in a Ratio of 1.1

(d) Analytical System

Optical System (i) Excitation Unit

The sensor platform is mounted on a computer-controlled adjustment module, allowing for translation in parallel and perpendicular to the grating lines and for rotation around an axis in parallel to the grating lines and with center of motion in the main axis of the area illuminated by the excitation light beam launched onto the grating structure (I) for incoupling into the sensor platform named in example 2(b). Immediately after the laser acting as an excitation light source, there is a shutter positioned in the light path in order to block the light path when measurement data is not being collected. Additionally, neutral density filters or polarizers can be mounted at this or also other positions in the path of the excitation light towards the sensor platform in order to vary the excitation light intensity step-wise or continuously.

The excitation light beam from a helium neon laser (2 mW) is expanded to a light beam of slit-type cross section (in parallel to the grating lines of the sensor platform) using a cylindrical lens. The peripheral upper and lower regions of the excitation light beam are masked by a slit diaphragm, the excitation light beam being slightly divergent in parallel to the grating lines, but parallel in the projection normal to the grating lines.

The resulting light bundle with slit-type cross section on the grating structure is directed onto the right edge of the incoupling grating in one of the sample compartments. The excitation light spot has a size of about 0.8 mm length×4 mm width. The sensor platform is adjusted for maximum incoupling, which is confirmed by a maximum intensity of the scattered light emitted (by scattering) along the guided mode of incoupled excitation light. This maximum can be determined both by visual inspection and by imaging of the light scattered along the guided mode, collected by an imaging system, onto an optoelectronic detector, for example, onto the pixels of a CCD-camera, as an example of a laterally resolving detector, or onto a photodiode, as an example of a laterally not resolving detector. Under the same conditions, a maximum signal is also determined for the excitation light transmitted in the waveguide and outcoupled at the outcoupling grating. A value of 3.8° is determined for the resonance angle for incoupling.

As a second excitation light source, a green helium neon laser with emission at 543 nm is used. The excitation light beam can be directed into the same optical light path as the red beam (633 nm) of the helium neon laser described above, the optical path of which is then blocked, using a mirror which can be flapped both manually and actuated by a motor between fixed positions. The adjustment of the resonance angle for incoupling is performed in the same way as described above, wherein a value of 15° is determined.

(ii) Detection

A CCD camera (TE3/A Astrocam, Cambridge, UK) with peltier cooling (operation temperature: −30° C.) is used as a laterally resolving detector. Signal collection and focusing onto the CCD chip is performed by means of a Heligon Tandem objective (Rodenstock, 2× Cine-Heligon 2.1/100 mm). Two interference filters (Omega Optical, Brattleborough, Vt.), with central wavelength of 680 nm and 40 nm bandwidth, and either a neutral density filter (for transmission of attenuated, scattered excitation light and of much weaker luminescence light from the measurement areas) or a neutral density filter in combination with an interference filter (for transmission of the attenuated excitation light from the measurement areas) are mounted on a filter wheel between the two parts of the Heligon Tandem objective. The signals at the excitation and the emission wavelength are measured alternately. Data analysis is performed using commercially available image analysis software (ImagePro Plus).

(e) Method of Luminescence Detection of the Hybridization Reaction:

Each of the 96 micro flow cells is filled individually with the biological material prepared according to the method described above using the laboratory robot. In a first thermal step (temperature increase to 85° C. for 30 min), the double-stranded cDNAs immobilized on the surface are dehybridized (separated) and thus prepared for hybridization with the Cy5-labeled or Cy3-labeled, single-stranded cDNAs in the sample, respectively. Hybridization of immobilized single-stranded cDNA with complementary Cy5-labeled, respectively Cy3-labeled molecules is enabled under so-called stringent conditions (hybridization of only completely complementary single strands), however without preferring kinetically or thermodynamically either of the differently labeled molecules, upon slow cooling down to 43° C. (about 2° C. per minute) and then thermal equilibration at 43° C. for 8 hours. In another step, the surmounting liquid is exchanged by pure hybridization buffer using the laboratory robot in order to remove non-bound material that can be excited to fluorescence, as well as material nonspecifically bound to the surface.

After the luminescence measurement, 2-molar urea, as a chaotropic reagent for regeneration, may be supplied by the laboratory robot. This (regeneration) process is accomplished by an increase of the temperature to 80° C. After another flushing with 10 mM phosphate buffer and re-equilibration in pure hybridization buffer, the fluidic/array system can be re-used.

For the (optical) read-out of the arrays in the individual sample compartments, the device described above is inserted into the disclosed analytical system and adjusted to maximum incoupling of excitation light (first of 633 nm) in the array of the first of the 96 sample compartments, as described above, which is controlled at the position of the filter-wheel for transmission of the excitation wavelength. Then, the intensity of the fluorescence light from the measurement areas (spots) is measured with the position of the filter-wheel for transmission at the luminescence wavelength (first with filter 680 DF 40, Omega Optical, Brattleborough, Vt., for Cy5). Read-it of the arrays in the other sample compartments is performed sequentially (always for one sample compartment after the other, with 100 measurement areas each), upon transfer of the device to the next position for read-out of the luminescence signals from the next sample compartment.

Then, the device is returned to the incoupling position for the array in the first sample compartment and, after flapping the mirror, adjusted to maximum incoupling of the green excitation light (543 nm). Then the intensity of the fluorescence light from the measurement areas (spots) of the array is measured with position of the filter-wheel for transmission at the shorter-wavelength luminescence (with filter 580 DF 40, Omega Optical, Brattleborough, Vt., for Cy3). Read-it of the arrays in the other sample compartments is performed sequentially (always for one sample compartment after the other, with 100 measurement areas each), upon transfer of the device to the next position for read-out of the luminescence signals from the next sample compartment.

Example 3

Device and Method for the Simultaneous Quantitative Determination of Multiple Cytokine Marker Proteins in One and in Multiple Samples (Multi-Cytokine Plate)

(a) As a device, a square sensor platform with the exterior dimensions of 101.6 mm×101.6 mm (4 inch×4 inch)×0.7 mm thickness is used, joined with a PDMS layer (polydimethylsiloxane, Sylgard 184 Silicon Elastomer Kit, Dow Corning) of 5 mm thickness, in which circular openings of 7 mm diameter each, in a (center-to-center) distance of 9 mm had been formed, for providing the sample compartments to receive the analysis volumes (10 μl-100 μl). The openings in the layer are arranged in a geometry of 11 rows and 11 columns (a total of 121 wells). For suppression of scattered light, the polymer material was inked with black pigment.

The substrate material (optically transparent layer (b)) consists of AF 45 glass (refractive index n=1.52 at 633 nm). A continuous structure of a surface relief grating, with a period of 360 nm and a grating depth of 25+/−5 nm, is generated in the substrate, with the orientation of the grating lines in parallel to the edge of the sensor platform. The waveguiding, optically transparent layer (a) of $Ta_2O_5$ on the optically transparent layer (b) has a refractive index of 2.15 at 633 nm (layer thickness 150 nm). Due to the deposition process, the grating structure is transferred into the surface of the waveguiding layer almost 1:1 according to scale.

The surface of the sensor platform is cleaned upon exposure to oxygen plasma in order to remove organic contaminations. Then an adhesion-promoting layer, comprising a monolayer of mono-octadecylphosphate, is deposited on the hydrophilic waveguide surface by a self-assembly process. This surface modification leads to a very hydrophobic surface (contact angle 100°-110° against water). The process of the surface modification is described in more detail in the literature (D. Brovelli et al., *Langmuir* 15 (1999) 4324-4327).

121 arrays (arranged in 11 rows×11 columns) of 25 spots each, with different antibodies as biological recognition elements for the recognition and binding of cytokine marker proteins, are deposited on the hydrophobic surface of the sensor platform coated with the adhesion-promoting layer using an inkjet plotter, model NPIC (GeSim GmbH, Groβ-erkmannsdorf, DE), the arrays being arranged in a geometry of 5 rows×5 columns each.

(b) The antibodies are deposited at a concentration of 100 µg/ml in sugar-containing (0.1% trehalose, phosphate-buffered silane (pH 7.4)), incubated in liquid state in an atmosphere of saturated water vapor for 2-3 hours, then washed and blown dry with nitrogen. The average diameter of the spots, in a (center-to-center) distance of 1 mm, is 0.5 mm. Five different antibodies for the recognition of cytokines, especially of different interleukins, are used in the always 5 rows of an individual array. In each array, 5 measurement areas with the same interleukin-antibodies as biological recognition elements are provided in order to generate data about the statistical assay reproducibility already from every individual measurement with a sample to supplied. Thereby, the position of the measurement area with the respective interleukin-antibody as the biological recognition element (in the array) is determined by a statistic algorithm, so that, at the end of the immobilization step, the positions of the 5 different interleukin-antibodies in the 25-spot array are known, but pre-determined in a purely statistical way. Thus, a significant reduction of analysis time and required amount of sample, in comparison to the described known analysis methods (e.g., ELISA), can be achieved in the following analysis step, these known analysis methods generally requiring a multitude of individual measurements in discrete sample compartments and, due to the large number of necessary individual measurements, also the use of multiple microtiter plates, for a determination of the assay reproducibility.

The remaining hydrophobic surface (of the sensor platform) not covered with proteins is blocked with 10 mg/ml serum albumin (incubation time 10 min) in order to suppress nonspecific binding of secondary antibodies during the later analysis step. After termination of the antibody immobilization, the prepared sensor platform is joined with PDMS layer in such a way that always one array is located within each of the 121 openings of the PDMS layer.

(c) Analytical System

Optical System (i) Excitation Unit

The sensor platform is mounted on a computer-controlled adjustment module allowing for translocation in parallel and perpendicular to the grating lines and for rotation around an axis in parallel to the grating lines and with center of motion in the main axis of the area illuminated by the excitation light beam launched onto the grating structure (I) for incoupling into the sensor platform named in example 3(a). Immediately after the laser acting as an excitation light source, there is a shutter positioned in the light path in order to block the light path when measurement data is not to be collected. Additionally, neutral density filters or polarizers can be mounted at this or also other positions in the path of the excitation light towards the sensor platform in order to vary the excitation light intensity step-wise or continuously.

The excitation light beam from a helium neon laser, at 632.8 nm, is expanded to a parallel ray bundle of circular cross-section with 25 mm diameter by means of 25-fold expansion optics. From the central part of this excitation light bundle, a square area of 16 mm length×16 mm width (in accordance with the nomenclature for the grating structure) is selected and, after passing a dichroic mirror (650 DRLP, Omega Optical, Brattleborough, Vt., USA), directed through the optically transparent layer (a) onto a group of 4 of the 121 arrays located in the central part of the excitation light spot. The sensor platform is adjusted for maximum incoupling, which is confirmed by a minimum of the transmission of excitation light through the sensor platform and by a maximum of the sum of reflected excitation light and of excitation light outcoupled by the continuous grating structure (c), after incoupling, under the same angle as the reflected light, within the measurement precision. The optimum incoupling angle can be determined both by visual inspection and, under computer control, from the signals of photodiodes connected to amplifiers, which photodiodes are positioned in the related light paths. In this way, an angle of 3.5° is determined as the resonance angle for incoupling.

(ii) Detection

A CCD camera (TE3/A Astrocam, Cambridge, UK) with peltier cooling (operation temperature: −30° C.) is used as a laterally resolving detector. Signal collection and focusing onto the CCD chip is performed by means of a Heligon Tandem objective (Rodenstock, 2× Cine-Heligon 2.1/100 mm). Two interference filters (Omega Optical, Brattleborough, Vt.), with central wavelength of 680 nm and 40 nm bandwidth, and either a neutral density filter (for transmission of attenuated, scattered excitation light and of much weaker luminescence light from the measurement areas) or a neutral density filter in combination with an interference filter (for transmission of the attenuated excitation light from the measurement areas) are mounted on a filter wheel between the two parts of the Heligon Tandem objective. The signals at the excitation and the emission wavelength are measured alternately. Data analysis is performed using commercially available image analysis software (ImagePro Plus).

(d) Analysis Method

For the specific recognition of the cytokines to be determined, the format of sandwich assay is chosen. For each of the selected interleukins (interleukins IL#1 to IL#5), 11 calibration solutions in phosphate-buffered saline, with additions of 0.1% serum albumin and 0.05% Tween 20 are prepared (interleukin concentrations: 0, 0.5, 1, 2, 5, 10, 20, 50, 100, 200, 300 pg/ml). Additionally, 11 mixed calibration solutions of all 5 interleukins are prepared, comprising each of the 5 interleukins at the same concentration, and, generated in a statistical (mixing) method, 55 sample solutions containing unknown concentrations of the interleukins. Then, the individual calibration solutions were pre-incubated with the corresponding specific, biotinylated secondary interleukin-antibody (always 200 picomolar) for one hour. Similarly, the mixed calibration solutions and the sample solutions were pre-incubated with a mixture of the 5 different biotinylated secondary interleukin-antibody (each 200 picomolar) for also one hour.

Then, 50 µl of the individual calibration solutions were filled into the first 5 rows of sample compartments on the sensor platform, allowing for generation of one individual calibration curve (dose-response curve) per interleukin in each row in the following analysis step of fluorescence determination. 50 µl of the mixed calibration solutions are filled into every one of the 11 sample compartments in the $6^{th}$ row in order to generate later on the corresponding calibration curves in the presence of the analyte mixture. In a corresponding way, the 55 sample solutions are distributed over the remaining rows of sample compartments. The incubation time for all 121 measurement solutions is 30 min. In the following, the sample compartments are washed with a buffer (phosphate-buffered saline with an addition of 0.1% serum albumin and 0.05% Tween 20). In the final analysis step by fluorescence determination, 50 µl of 1-nanomolar Cy5-streptavidin (Amersham Pharmacia) in buffer solution (phosphate-buffered saline with an addition of 0.1% serum albumin and 0.05% Tween 20) are filled into each sample compartment, and the fluorescence signals from all the measurement areas in the 121 arrays are measured after another 15 min incubation time.

For the (optical) read-out of the arrays in the individual sample compartments, the device described above is inserted into the disclosed analytical system and adjusted to maximum incoupling of excitation light in the arrays of the first 4 of the 96 sample compartments, as described above, which is controlled at the position of the filter-wheel for transmission of the excitation wavelength. Then, the intensity of the fluorescence light from the measurement areas (spots) is measured with position of the filter-wheel for transmission at the luminescence wavelength. Read-it of the arrays in the other sample compartments is performed sequentially (always for a group of 4 sample compartments with 25 discrete measurement areas each), upon transfer of the device to the next position for read-out of the luminescence signals from the next sample compartment.

The invention claimed is:

1. A device comprising:
   a sensor platform having one planar optical waveguide wherein the planar optical waveguide has a plurality of waveguide regions;
   a sealing layer forming, either directly or with a sealing medium, a tight seal with said planar optical waveguide; and
   a plurality of recesses opening at least towards said sensor platform, which form a corresponding plurality of sample compartments, said plurality of sample compartments being arranged with at least two sample compartments in a length direction and at least two sample compartments in a width direction, wherein
   each of said sample compartments comprises only a single waveguide region and has different biological or biochemical recognition elements for specific recognition and binding of different analytes immobilized in five or more discrete measurement areas on said planar optical waveguide, said measurement areas being arranged with at least two measurement areas in a length direction and at least two measurement areas in a width direction,
   said measurement areas are in optical interaction with excitation light emanating from said optical waveguide, as part of said sensor platform which forms a demarcation of said sample compartments, and
   said sample compartments are operable to have sample or reagent solutions received therein cleared therefrom and to have further sample or reagent solutions supplied thereto.

2. A device according to claim 1, wherein at least one of said measurement areas in each of said sample compartments is for referencing.

3. A device according to claim 2, wherein said referencing measurement areas reference same chemical or optical parameters in a number of said sample compartments distributed over said sensor platform, whereby a lateral distribution of the chemical or optical parameters over said sensor platform is determined.

4. A device according to claim 1, wherein said measurement areas are in optical interaction with an evanescent field of the excitation light guided in said planar optical waveguide.

5. A device according to claim 1, wherein said planar optical waveguide is a multi-mode or single-mode waveguide comprising an anorganic material or an organic material that is optically transparent at least at an excitation wavelength and a luminescence wavelength.

6. A device according to claim 1, wherein said planar optical waveguide is self-supporting.

7. A device according to claim 1, wherein said planer optical waveguide is an optical film waveguide having a first optically transparent layer and a second optically transparent layer, said first optically transparent layer being on said second optically transparent layer and said second optically transparent layer having a lower refractive index than said first optically transparent layer.

8. A device according to claim 7, wherein said second optically transparent layer comprises glass, quartz, or transparent thermoplastic plastics.

9. A device according to claim 7, wherein the refractive index of said first optically transparent layer is higher than 1.8.

10. A device according to claim 7, wherein said first optically transparent layer comprises $TiO_2$, $ZnO$, $Nb_2O_5$, $Ta_2O_5$, $HfO_2$, or $ZrO_2$.

11. A device according to claim 7, wherein a thickness of said first optically transparent layer is between 40 and 300 nm.

12. A device according to claim 7, wherein said optical film waveguide further has an additional optically transparent layer in contact with said first optically transparent layer and having a lower refractive index than said first optically transparent layer, said additional optically transparent layer having a thickness of 5 nm-10,000 nm and being located between said first and second optically transparent layers.

13. A device according to claim 12, wherein said additional optically transparent layer reduces surface roughness below said first optically transparent layer, reduces penetration of an evanescent field, of light guided in said first optically transparent layer, into one or more layers located below said first optically transparent layer, improves adhesion of said first optically transparent layer to the one or more layers located below said first optically transparent layer, reduces thermally induced stress within said sensor platform, or provides chemical isolation of said first optically transparent layer from layers located below, by sealing of micro pores in said first optically transparent layer against the layers located below.

14. A device according to claim 7, further comprising an adhesion-promoting layer deposited on said first optically transparent layer for immobilizing biological, biochemical or synthetic recognition elements.

15. A device according to claim 14, wherein said adhesion-promoting layer has a thickness of less than 200 nm.

16. A device according to claim 14, wherein said adhesion-promoting layer comprises chemical compounds of a group consisting of silanes, epoxides, and self-organized functionalized monolayers.

17. A device according to claim 1, wherein said measurement areas are generated by deposition of biological, biochemical or synthetic recognition elements on said sensor platform.

18. A device according to claim 17, wherein said measurement areas are deposited by one or more methods of a group consisting of ink jet spotting, mechanical spotting by means of pin or pen, micro contact printing, fluidic contacting of said measurement areas with the biological, biochemical or synthetic recognition elements upon their supply in parallel or crossed micro channels, upon application of pressure differences or of electric or electromagnetic potentials.

19. A device according to claim 17, wherein, as the biological, biochemical or synthetic recognition elements, components of a group consisting of nucleic acids, antibodies, aptamers, membrane-bound and isolated receptors, ligands of the membrane-bound and isolated receptors, antigens for antibodies, histidin-tag components, cavities generated by chemical synthesis, for hosting molecular imprints, are deposited.

20. A device according to claim 17, wherein whole cells or cell fragments are deposited as the biological, biochemical or synthetic recognition elements.

21. A device according to claim 17, wherein compounds, which are chemically neutral towards the analytes, are deposited between said measurement areas, in order to minimize nonspecific binding or adsorption.

22. A device according to claim 21, wherein the compounds, which are chemically neutral towards the analyte, are albumines, herring sperm, or polyethyleneglycols.

23. A device according to claim 7, wherein said first optically transparent layer has at least one grating structure formed therein for incoupling excitation light to said measurement areas.

24. A device according to claim 7, wherein said first optically transparent layer has at least one grating structure formed therein for outcoupling light guided in said first optically transparent layer.

25. A device according to claim 23, wherein said first optically transparent layer also has at least one grating structure formed therein for outcoupling light guided in said first optically transparent layer.

26. A device according to claim 25, wherein said incoupling and outcoupling grating structures are interchangeable with respect to incoupling and outcoupling.

27. A device according to claim 25, wherein said incoupling and outcoupling grating structures have a period of 200 nm-1000 nm and a grating modulation depth of 3 nm-100 nm.

28. A device according to claim 27, wherein a ratio of the grating modulation depth to a thickness of said first optically transparent layer is equal or smaller than 0.2.

29. A device according to claim 23, wherein said grating structure is also for outcoupling, said grating structure being (a) a relief grating with a rectangular, triangular or semicircular profile or (b) a phase or volume grating with a periodic modulation of a refractive index in said first optically transparent layer.

30. A device according to claim 7, further comprising a thin metal layer deposited between said first optically transparent layer and the immobilized biological or biochemical recognition elements, wherein a thickness of said thin metal layer is such that a surface plasmon at least one of an excitation wavelength and a luminescence wavelength is excitable.

31. A device according to claim 23, wherein said grating structure is also for outcoupling, said grating structure being a diffractive grating with a uniform period.

32. A device according to claim 23, wherein said grating structure is a multi-diffractive grating.

33. A device according to claim 25, wherein said incoupling and outcoupling grating structures are located outside a region of said sample compartments.

34. A device according to claim 25, wherein said incoupling and outcoupling grating structures extend over at least a portion of said sample compartments.

35. A device according to claim 23, wherein a portion of said sealing layer is optically transparent both for excitation radiation and excited luminescence radiation at least within a penetration depth of an evanescent field.

36. A device according to claim 35, wherein said sealing layer comprises a first layer that is in contact with a surface of said sensor platform, said first layer being transparent for the excitation radiation and the excited luminescence radiation, and a second layer that is located remote from said sensor platform, said second layer being absorbent in a spectral range of the excitation radiation and of the excited luminescence radiation.

37. A device according to claim 34, wherein said sealing layer is absorbent in a spectral range of excitation radiation and excited luminescence radiation.

38. A device according to claim 1, wherein said sealing layer is self-adhesive.

39. A device according to claim 1, wherein said sealing layer comprises a polysiloxane.

40. A device according to claim 1, wherein 5-1000 of said measurement areas are located in one of said sample compartments.

41. A device according to claim 1, wherein an individual one of said measurement areas in said sample compartments occupies an area of 0.001-6 mm$^2$, and wherein different measurement areas have similar or different sizes.

42. A device according to claim 1, wherein each of said sample compartments has a volume of 100 nl-1 ml.

43. A device according to claim 1, wherein said sample compartments are closed at a side facing away from said sensor platform except for inlet and outlet openings for supply and removal, respectively, of samples, wherein the supply and removal of the samples is performed in a closed flow-through system, and wherein when liquid is supplied to said measurement areas or segments with common inlet and outlet openings, said inlet and outlet openings are addressed row by row or column by column.

44. A device according to claim 1, wherein the supply of the samples is performed in parallel or crossed micro channels, affected by pressure differences or by electric or electromagnetic potentials.

45. A device according to claim 1, wherein said sample compartments have openings for locally addressed supply or removal of samples or other reagents at a side facing away from said sensor platform.

46. A device according to claim 1, wherein compartments are provided for reagents, which are wetted and brought into contact with said measurement areas during an assay.

47. A device according to claim 1, wherein said sensor platform has optically or mechanically recognizable marks provided thereon, the optically or mechanically recognizable marks at least one of facilitating adjustment of said sensor platform in an optical system and facilitating combination of said sensor platform with said sealing layer having said recesses for said sample compartments.

48. An analytical system for the determination of one or more luminescences, the analytical system comprising:
   at least one excitation light source;
   a device according to claim 1; and
   at least one detector for recording emission light emanating from at least one of said measurement areas on said sensor platform.

49. An analytical system according to claim 48, wherein said planar optical waveguide is an optical film waveguide having a first optically transparent layer and a second optically transparent layer, said first optically transparent layer being on said second optically transparent layer and said second optically transparent layer having a lower refractive index than said first optically transparent layer, and wherein the excitation light emitted by said at least one excitation light source is coherent and directed onto one or more of said measurement areas at a resonance angle for incoupling into said first optically transparent layer.

50. An analytical system according to claim 49, further comprising expansion optics, wherein said expansion optics expand the excitation light of said at least one light source to an essentially parallel ray bundle and direct the essentially parallel ray bundle onto said one or more measurement areas at the resonance angle for incoupling into said first optically transparent layer.

51. An analytical system according to claim 49, further comprising at least one diffractive optical element, wherein said at least one diffractive optical element divides the excitation light from said at least one light source into a multitude of individual beams having similar intensities, the individual beams being directed essentially in parallel to each other onto laterally separated measurement areas.

52. An analytical system according to claim 49, wherein said at least one excitation light source is at least two coherent light sources.

53. An analytical system according to claim 48, wherein said at least one detector is a laterally resolving detector.

54. An analytical system according to claim 53, wherein said laterally resolving detector is a CCD camera, a CCD chip, a photodiode array, an Avalanche diode array, a multi-channel plate, or a multi-channel photomultiplier.

55. An analytical system according to claim 48, further comprising optical components located at least one of between said excitation light source and said detector and said sensor platform and said detector, said optical components including at least two of (a) lenses or lens systems for shaping of transmitted light bundles, (b) planar or curved mirrors for deviation of the transmitted light bundles, (c) prisms for deviation and optionally spectral separation of the transmitted light bundles, (d) dichroic mirrors for spectrally selective deviation of parts of the transmitted light bundles, (e) neutral density filters for regulation of transmitted light intensity, (f) optical filters or monochromators for spectrally selective transmission of parts of the transmitted light bundles, and (g) polarization selective elements for selection of discrete polarization directions of the excitation light or luminescence light.

56. An analytical system according to claim 48, wherein said excitation light source emits the excitation light in pulses with a duration of 1 fsec to 10 min.

57. An analytical system according to claim 48, wherein the emission light from said at least one measurement area is measured time-resolved.

58. An analytical system according to claim 48, wherein light signals of the excitation light at a location of said excitation light source, the excitation light after expansion, the excitation light after its multiplexing into individual beams, scattered light at an excitation wavelength from a location of one or more laterally separated measurement areas, or light of the excitation wavelength outcoupled by a grating structure are measured for reference.

59. An analytical system according to claim 58, wherein said measurement areas for determination of the emission light and of the reference light signals are identical.

60. An analytical system according to claim 48, wherein launching of the excitation light and detection of the emission light from said at least one measurement area is performed sequentially for one or more of said sample compartments.

61. An analytical system according to claim 60, further comprising movable optical components for performing the sequential excitation and detection, said movable optical components including at least two of mirrors, deviating prisms, and dichroic mirrors.

62. An analytical system according to claim 61, further comprising an essentially focus and angle preserving scanner for performing the sequential excitation and detection.

63. An analytical system according to claim 60, wherein said sensor platform is moved between steps of sequential excitation and detection.

64. A device according to claim 7, wherein said measurement areas are generated by deposition of biological, biochemical or synthetic recognition elements on said sensor platform.

65. A device according to claim 7, wherein said sealing layer is self-adhesive.

66. A device according to claim 7, wherein said sealing layer comprises a polysiloxane.

67. A device according to claim 7, wherein 5-1000 of said measurement areas are located in one of said sample compartments.

68. A device according to claim 7, wherein an individual one of said measurement areas in said sample compartments occupies an area of 0.001-6 mm$^2$, and wherein different measurement areas have similar or different sizes.

69. A device according to claim 7, wherein each of said sample compartments has a volume of 100 nl-1 ml.

70. A device according to claim 7, wherein said sample compartments are closed at a side facing away from said first optically transparent layer except for inlet and outlet openings for supply and removal, respectively, of samples, wherein the supply and removal of the samples is performed in a closed flow-through system, and wherein a liquid is supplied to said measurement areas or segments with common inlet and outlet openings, said inlet and outlet openings being addressed row by row or column by column.

71. A device according to claim 7, wherein the supply of the samples is performed in parallel or crossed micro channels, affected by pressure differences or by electric or electromagnetic potentials.

72. A device according to claim 7, wherein said sample compartments have openings for locally addressed supply or removal of samples or other reagents at a side facing away from said first optically transparent layer.

73. A device according to claim 7, wherein compartments are provided for reagents, which are wetted and brought into contact with said measurement areas during an assay.

74. A device according to claim 7, wherein said sensor platform has optically or mechanically recognizable marks provided thereon, the optically or mechanically recognizable marks at least one of facilitating adjustment of said sensor platform in an optical system and facilitating combination of said sensor platform with said sealing layer having said recesses for said sample compartments.

75. An analytical system for determining one or more luminescences, the analytical system comprising:
 at least one excitation light source;
 a device according to claim 7; and
 at least one detector for recording emission light emanating from at least one of said measurement areas on said sensor platform.

\* \* \* \* \*